United States Patent
Suzuki et al.

(10) Patent No.: US 7,094,935 B2
(45) Date of Patent: Aug. 22, 2006

(54) ADSORBENT FOR PURIFYING PERFLUOROCARBON, PROCESS FOR PRODUCING SAME, HIGH PURITY OCTAFLUOROPROPANE AND OCTAFLUOROCYCLOBUTANE, AND USE THEREOF

(75) Inventors: Yasuhiro Suzuki, Kawasaki (JP); Hiroshi Atobe, Kawasaki (JP); Minako Horiba, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 430 days.

(21) Appl. No.: 10/363,215

(22) PCT Filed: Sep. 14, 2001

(86) PCT No.: PCT/JP01/07988

§ 371 (c)(1),
(2), (4) Date: Mar. 6, 2003

(87) PCT Pub. No.: WO02/22254

PCT Pub. Date: Mar. 21, 2002

(65) Prior Publication Data

US 2003/0181315 A1   Sep. 25, 2003

Related U.S. Application Data

(60) Provisional application No. 60/241,742, filed on Oct. 20, 2000, provisional application No. 60/241,744, filed on Oct. 20, 2000.

(30) Foreign Application Priority Data

Sep. 14, 2000  (JP)  .............................. 2000-279315
Sep. 14, 2000  (JP)  .............................. 2000-279394

(51) Int. Cl.
   *C07C 17/38*   (2006.01)
   *B01J 20/34*   (2006.01)
   *B01J 38/02*   (2006.01)
   *B01J 21/18*   (2006.01)

(52) U.S. Cl. .................. 570/177; 570/179; 502/56; 502/180

(58) Field of Classification Search .............. None
See application file for complete search history.

(56) References Cited

U.S. PATENT DOCUMENTS

| 3,004,075 A | 10/1961 | Marcali |
| 3,026,359 A | 3/1962 | Mastrangelo |
| 5,364,821 A | 11/1994 | Holland |
| 5,417,742 A | 5/1995 | Tamhankar et al. |
| 6,815,568 B1 * | 11/2004 | Horiba et al. ............... 570/179 |

FOREIGN PATENT DOCUMENTS

| EP | 0 663 370 A1 | 7/1995 |
| GB | 2 311 522 A | 10/1997 |
| JP | 60-81134 A | 5/1985 |
| JP | 8-47638 A | 2/1996 |
| WO | WO 99/44973 A | 9/1999 |

OTHER PUBLICATIONS

DATABASE WPI. Section Ch, Week 199441. Derwent Publications Ltd., London, GB; AN 1994-329775 XPOO2204515.

* cited by examiner

*Primary Examiner*—Sikarl A. Witherspoon
(74) *Attorney, Agent, or Firm*—Sughrue Mion, PLLC

(57) ABSTRACT

To provide a purification adsorbent capable of effectively removing impurities contained in a perfluorocarbon and obtaining a perfluorocarbon reduced in the impurity content to 1 ppm by mass or less; a process for producing the adsorbent; high-purity octafluoropropane or octafluorocyclobutane; processes for purifying and for producing the octafluoropropane or octafluorocyclobutane; and uses thereof. Purification is performed using a purification adsorbent produced by a method comprising (1) washing an original coal with an acid and then with water, (2) deoxidizing and/or dehydrating the original coal, (3) re-carbonizing the original coal at a temperature of from 500 to 700° C. and (4) activating the original coal at a temperature of from 700 to 900° C. in a mixed gas stream containing an inert gas, carbon dioxide and water vapor.

30 Claims, No Drawings

ADSORBENT FOR PURIFYING PERFLUOROCARBON, PROCESS FOR PRODUCING SAME, HIGH PURITY OCTAFLUOROPROPANE AND OCTAFLUOROCYCLOBUTANE, AND USE THEREOF

CROSS REFERENCE TO THE RELATED APPLICATIONS

This application is a 371 of PCT/JP01/07988, filed Sep. 14, 2001 and published as WO 02/22254 on Mar. 21, 2002.

This is an application based on the prescription of 35 U.S.C. Section 111(a) with claiming the benefit of filing date of U.S. Provisional applications Ser. No. 60/241,742 filed Oct. 20, 2000 and Ser. No. 60/241,744 filed Oct. 20, 2000 under the provision of 35 U.S.C. 111(b), pursuant to 35 U.S.C. Section 119(e)(1).

TECHNICAL FIELD

The present invention relates to an adsorbent for purifying perfluorocarbon, a process for producing the adsorbent, high-purity octafluorpropane and octafluorocyclobutane, processes for purifying and for producing the octafluorpropane or octafluorocyclobutane, and uses thereof.

BACKGROUND OF THE INVENTION

Perfluorocarbon such as octafluoropropane (hereinafter referred to as "FC-218") or octafluorocyclobutane (hereinafter referred to as "FC-C318") is used as an etching gas or a cleaning gas in the process of manufacturing a semiconductor device.

For producing FC-218, a method of electrolytically fluorinating 1-chloropropane (see, U.S. Pat. No. 3,709,800), a method of reacting trifluoropentachloropropane and manganese trifluoride (see, U.S. Pat. No. 2,578,721) and a method of reacting propane or propylene with hydrogen fluoride and chlorine (see, U.S. Pat. No. 5,220,083) are known. However, these methods use a compound containing chlorine as a starting material and therefore, have a problem in that chlorine-containing impurities are yielded as by-products.

With respect to the method using a starting material or the like free of chlorine, a method of electrolytically fluorinating propane (see, U.S. Pat. No. 3,840,0445) is known, however, the apparatus therefor is very complicated and the yield is low, therefore, this is not an industrially advantageous method. Also, a method of fluorinating hexafluoropropene (hereinafter referred to as "FC-1216") to produce FC-218 is known. For example, a method of reacting FC-1216 with a fluorine gas under dilution with an inert gas and a reaction product gas (see, JP-B-62-61682) (the term "JP-B" as used herein means an "Japanese Examined Patent Publication (Kokoku)"), a method of electrolytically fluorinating FC-1216 in hydrogen fluoride (see, JP-B-62-61115), and a method of reacting a high-order metal fluoride containing at least one member selected from cobalt trifluoride, manganese trifluoride and silver difluoride (see, JP-B-62-54777) are known.

For producing FC-1216, a method of using thermal decomposition of chlorodifluoromethane (hereinafter referred to as "HCFC-22") is known. In addition, a method of fluorinating perhalogenated C-3 chlorofluorocarbon and then dehalogenating the fluorination product to produce FC-1216 (see, U.S. Pat. No. 5,057,634) is known. These methods also use a chlorine-containing compound as a starting material, therefore, FC-1216 contains a chlorine-containing compound as impurities in many cases and FC-218 produced starting from this FC-1216 contains chlorine-containing impurities together with unreacted FC-1216 in many cases. The boiling points of chlorine-containing impurities are shown in Table 1. The impurities can be mostly separated by distillation, however, the boiling points of chloropentafluoroethane (hereinafter referred to as "CHF-115") and FC-1216 each is approximated to the boiling point of FC-218 and therefore, separation of these impurities by distillation is very difficult.

TABLE 1

| Compound Name | Structural Formula | Boiling Point (° C.) |
|---|---|---|
| Octafluoropropane (FC-218) | $CF_3CF_2CF_3$ | −36.7 |
| Hexafluoropropene (FC-1216) | $CF_3CF=CF_2$ | −31 |
| Chlorodifluoromethane (HCFC-22) | $CHClF_2$ | −41 |
| 2-Chloro-1,1,1,2-tetrafluoroethane (HCFC-124) | $CF_3CHClF$ | −12 |
| Chloro-1,1,2,2-tetrafluoroethane (HCFC-124a) | $CHF_2CClF_2$ | −10.2 |
| 1H-Heptafluoropropane (HFC-227ca) | $CHF_2CF_2CF_3$ | −19 |
| Chloropentafluoroethane (CFC-115) | $CClF_2CF_3$ | −38.7 |
| 1,2-Dichlorotetrafluoroethane (CFC-114) | $CClF_2CClF_2$ | −3.8 |
| Tetrafluoroetylene (FC-1114) | $CF_2=CF_2$ | −31 |
| Octafluorocyclobutane (FC-C318) | $c\text{-}CF_2CF_2CF_2CF_2\text{—}$ | −6 |

Similarly, octafluorocyclobutane (FC-C318) can be obtained by purifying FC-C318 yielded as a by-product at the production of tetrafluoroethylene (hereinafter referred to as "FC-1114") or hexafluoropropene (FC-1216). For producing FC-1114 or FC-1216, a method of thermally decomposing chlorodifluoromethane is used as described, for example, in EP451793, however, by the thermal decomposition reaction, many kinds of substances are produced. Also, unreacted HCFC-22 and many chlorine-containing compounds are contained in the product. The boiling points of FC-C318 and compounds contained as impurities are shown in Table 1. Most of these reaction products and unreacted HCFC-22 can be separated by distillation. However, the boiling points of FC-1216, 2-chloro-1,1,1,2-tetrafluoroethane (hereinafter referred to as "HCFC-124"), 1-chloro 1,1,2,2-tetrafluoroethane (hereinafter referred to as "HCFC-124a"), 1H-heptafluoropropane (hereinafter referred to as "HFC-227ca") and 1,2-dichlorotetrafluoroethane (hereinafter referred to as "CFC-114") each is approximated to the boiling point of FC-C318. Furthermore, HCFC-124 and HCFC-124a each produces an azeotropic mixture with FC-C318. Therefore, FC-C318 reduced in the concentration of these impurities to 1 ppm by mass or less can be hardly obtained by a purification method using separation by distillation.

Other than the separation by distillation, the purification method includes extractive distillation, membrane separation and adsorption separation. However, the extractive distillation method has a problem in that the equipment costs highly and the process is complicated. The membrane separation method has a problem in that an appropriate membrane having properties necessary for separating FC-218 or FC-C318 from impurities is not known and purification to an impurity content of 1 ppm by mass or less is unavailable. The molecular sizes (calculated values at stable state structure) of FC-218 or FC-C318 and their impurity compounds are shown in Table 2. The separation by adsorption using a known adsorbent such as activated carbon, silica gel, zeolite (Molecular Sieves) or Molecular Sieving Carbon (hereinafter referred to as "MSC"), can hardly attain the purification because there is almost no difference in the molecular size and boiling point between FC-218 or FC-318 and their impurities and furthermore, there is similarity in the physical properties between FC-218 or FC-C318 and their impurities.

TABLE 2

| Compound Name | Molecular Size (calculated value) |
|---|---|
| Octafluoropropane (FC-218) | 4.9 to 6.1 Å |
| Chloropentafluoroethane (CFC-115) | 4.3 to 5.6 Å |
| Hexafluoropropene (FC-1216) | 4.9 to 5.9 Å |
| Chloro-1,1,1,2-tetrafluoroethane (HCFC-124) | 4.3 to 5.6 Å |
| Chloro-1,1,2,2-tetrafluoroethane (HCFC-124a) | 4.3 to 5.6 Å |
| 1H-Heptafluoropropane (HFC-227ca) | 4.3 to 6.2 Å |
| 1,2-Dichlorotetrafluoroethane (CFC-114) | 4.8 to 5.6 Å |
| Octafluorocyclobutane (FC-C318) | 5.2 to 5.8 Å |

Activated carbon is effective in adsorbing and thereby removing FC-1216 which is one of impurities, but cannot separate all other impurities. In conventional purification methods, it has been particularly difficult to obtain FC-218 having a CFC-115 concentration of 1 ppm by mass or less or FC-318 having a HCFC-124 and HCFC-124a concentration of 1 ppm by mass or less.

The present invention has been made under these circumstances and the object of the present invention is to provide a purification adsorbent capable of effectively removing impurities contained in a perfluorocarbon which have been heretofore difficult to remove from a perfluorocarbon by conventional purification methods, in particular removing FC-1216, CFC-115, etc. from FC-218 and FC-1216, HCFC-124, HCFC-124a, HFC-227ca, CFC-114, etc. from FC-C318, and thereby obtaining a perfluorocarbon reduced in the contents of those impurities to 1 ppm by mass or less.

The object of the present invention includes providing an adsorbent for purification of a perfluorocarbon; a process for producing the adsorbent for purification of a perfluorocarbon; high-purity octafluorpropane or octafluorocyclobutane; processes for purifying and for producing the octafluorpropane or octafluorocyclobutane; and uses thereof.

DISCLOSURE OF THE INVENTION

As a result of extensive investigations to solve the above-described problems, the present inventors have found that when an original coal is washed with an acid to reduce metals, particularly alkali metals, contained in the original coal and then subjected to a series of activation treatments, the resulting activated char is an adsorbent having excellent properties of adsorbing the above-described impurities contained in perfluorocarbon. The present invention has been accomplished based on this finding. The present invention relates to the following matters [1] to [35].

[1] An adsorbent for purifying a perfluorocarbon, which is produced using a method comprising the following four steps:

(1) washing an original coal with an acid and then with water;

(2) deoxidizing and/or dehydrating the original coal obtained in the step (1) at a temperature of 50 to 250° C. in an inert gas stream;

(3) re-carbonizing the original coal obtained in the step (2) at a temperature of 500 to 700° C. in an inert gas stream; and (4) activating the original coal obtained in the step (3) at a temperature of 700 to 900° C. in a mixed gas stream containing an inert gas, carbon dioxide and water vapor.

[2] The adsorbent for purifying a perfluorocarbon as described in [1] above, wherein the original coal is obtained by carbonizing at least one member selected from the group consisting of coconut husk coal, coal, charcoal and tar pitch at a temperature of 400 to 600° C.

[3] The adsorbent for purifying a perfluorocarbon as described in [1] or [2] above, wherein the acid used in the acid washing of the step (1) is a mineral acid and the acid concentration is from 1 to 1,000 mol/m$^3$.

[4] The adsorbent for purifying a perfluorocarbon as described in any one of [1] to [3] above, wherein the acid used in the acid washing of the step (1) is hydrochloric acid and/or sulfuric acid.

[5] The adsorbent for purifying a perfluorocarbon as described in any one of [1] to [4] above, wherein the step (3) is performed by elevating the temperature up to the re-carbonization temperature of the step (3) at a rate of from 300 to 500° C./hr in an inert gas stream after the step (2).

[6] The adsorbent for purifying a perfluorocarbon as described in any one of [1] to [5] above, wherein the step (4) is performed by elevating the temperature up to the activation temperature of the step (4) at a rate of from 100 to 200° C./hr in an inert gas stream after the step (3).

[7] The adsorbent for purifying a perfluorocarbon as described in any one of [1] to [6] above, wherein in the step (4), the mixed gas containing an inert gas, carbon dioxide and water vapor contains from 50 to 89 vol % of the inert gas, from 10 to 30 vol % of carbon dioxide and from 1 to 20 vol % of water vapor.

[8] The adsorbent for purifying a perfluorocarbon as described in any one of [1] to [7] above, wherein the activated coal is cooled to room temperature at a rate of from 200 to 300° C./hr in an inert gas stream after the step (4).

[9] The adsorbent for purifying a perfluorocarbon as described in any one of [1] to [8] above, wherein the iodine adsorption quantity of the adsorbent is from 700 to 1,000 mg/g.

[10] The adsorbent for purifying a perfluorocarbon as described in any one of [1] to [9] above, wherein the total content of alkali metals in the adsorbent is 1,000 ppm or less.

[11] The adsorbent for purifying a perfluorocarbon as described in [10] above, wherein the potassium content in the adsorbent is 500 ppm or less.

[12] The adsorbent for purifying a perfluorocarbon as described in any one of [1] to [11] above, wherein the perfluorocarbon is octafluoropropane.

[13] The adsorbent for purifying a perfluorocarbon as described in any one of [1] to [12] above, wherein the perfluorocarbon is octafluorocyclobutane.

[14] A process for producing an adsorbent for purifying a perfluorocarbon, comprising the following four steps;

(1) washing an original coal with an acid and then with water;

(2) deoxidizing and/or dehydrating the original coal obtained in the step (1) at a temperature of from 50 to 250° C. in an inert gas stream;

(3) re-carbonizing the original coal obtained in the step (2) at a temperature of 500 to 700° C. in an inert gas stream; and (4) activating the original coal obtained in the step (3) at a temperature of from 700 to 900° C. in a mixed gas stream containing an inert gas, carbon dioxide and water vapor.

[15] The process for producing an adsorbent for purifying a perfluorocarbon as described in [14] above, wherein the original coal is obtained by carbonizing at least one member selected from the group consisting of coconut husk coal, coal, charcoal and tar pitch at a temperature of from 400 to 600° C.

[16] The process for producing an adsorbent for purifying a perfluorocarbon as described in [14] or [15] above, wherein the acid used in the acid washing treatment of the step (1) is a mineral acid and the acid concentration is from 1 to 1,000 mol/m$^3$.

[17] The process for producing an adsorbent for purifying a perfluorocarbon as described in any one of [14] to [16] above, wherein the acid used in the acid washing treatment of the step (1) is hydrochloric acid and/or sulfuric acid.

[18] The process for producing an adsorbent for purifying a perfluorocarbon as described in any one of [14] to [17] above, wherein the step (3) is performed by elevating the temperature up to the re-carbonization treatment temperature of the step (3) at a rate of from 300 to 500° C./hr in an inert gas stream after the step (2).

[19] The process for producing an adsorbent for purifying a perfluorocarbon as described in any one of [14] to [18] above, wherein the step (4) is performed by elevating the temperature up to the activation temperature of the step (4) at a rate of from 100 to 200° C./hr in an inert gas stream after the step (3).

[20] The process for producing an adsorbent for purifying a perfluorocarbon as described in any one of [14] to [19] above, wherein in the step (4), the mixed gas containing an inert gas, carbon dioxide and water vapor contains from 50 to 89 vol % of the inert gas, from 10 to 30 vol % of carbon dioxide and from 1 to 20 vol % of water vapor.

[21] The process for producing an adsorbent for purifying a perfluorocarbon as described in any one of [14] to [20] above, wherein the activated coal is cooled to room temperature at a rate of from 200 to 300° C./hr in an inert gas stream after the step (4).

[22] The process for producing an adsorbent for purifying perfluorocarbon as described in any one of [14] to [21] above, wherein the iodine adsorption quantity of the adsorbent is 700 to 1,000 mg/g.

[23] The process for producing an adsorbent for purifying a perfluorocarbon as described in any one of [14] to [22] above, wherein the total content of alkali metals in the adsorbent is 1,000 ppm or less.

[24] The process for producing an adsorbent for purifying a perfluorocarbon as described in [23] above, wherein the potassium content in the adsorbent is 500 ppm or less.

[25] The process for producing an adsorbent for purifying a perfluorocarbon as described in any one of [14] to [24] above, wherein the perfluorocarbon is octafluorocyclobutane or octafluoropropane.

[26] A process for purifying octafluorocyclobutane, comprising contacting crude octafluorocyclobutane containing from 10 to 10,000 ppm of impurities with the adsorbent for purifying a perfluorocarbon described in any one of [1] to [12] above to purify the crude octafluoropropane.

[27] The process for purifying the octafluoropropane as claimed in [26], wherein the impurities are at least one compound selected from the group consisting of chloropentafluoroethane, hexafluoropropene and 1H-heptafluoropropane.

[28] A process for purifying octafluorocyclobutane, comprising contacting crude octafluorocyclobutane containing from 10 to 10,000 ppm of impurities with the adsorbent for purifying perfluorocarbon described in any one of [1] to [11] and [13] to purify the crude octafluorocyclobutane.

[29] The process for purifying the octafluoro-cyclobutane as described in [28] above, wherein the impurities are at least one compound selected from the group consisting of 2-chloro-1,1,1,2-tetrafluoroethane, 1-chloro-1,1,2,2-tetrafluoroethane, 1,2-dichlorotetra-fluoroethane, 1H-heptafluoropropane and hexafluoropropene.

[30] A process for producing a high-purity octafluoropropane or octafluorocyclobutane, comprising the following steps (I) and (II);

(I) thermally decomposing chlorodifluoromethane to obtain crude octafluoropropane or octafluorocyclobutane; and (II) contacting the crude octafluoropropane or octafluorocyclobutane obtained in the step (I) with the adsorbent for purifying a perfluorocarbon described in any one of [1] to [13] to purify the crude octafluoropropane or octafluorocyclobutane.

[31] The process for producing high-purity octafluoropropane or octafluorocyclobutane as described in [30] above, wherein the purity of octafluorocyclobutane is 99.9999% by mass or more.

[32] An etching gas comprising octafluoropropane having a purity of 99.9999% by mass or more.

[33] An etching gas comprising octafluorocyclobutane having a purity of 99.9999% by mass or more.

[34] A cleaning gas comprising octafluoropropane having a purity of 99.9999% by mass or more.

[35] A cleaning gas comprising octafluorocyclobutane having a purity of 99.9999% by mass or more.

MODES OF CARRYING OUT THE INVENTION

The present invention is described in detail below.

The adsorbent for purifying perfluorocarbon of the present invention is characterized in that the adsorbent is produced using a method comprising the following four steps:

(1) washing an original coal with an acid and then with water;

(2) deoxidizing and/or dehydrating the original coal obtained in the step (1) at a temperature of 50 to 250° C. in an inert gas stream;

(3) re-carbonizing the original coal obtained in the step (2) at a temperature of from 500 to 700° C. in an inert gas stream; and (4) activating the original coal obtained in the step (3) at a temperature of from 700 to 900° C. in a mixed gas stream containing an inert gas, carbon dioxide and water vapor.

The adsorbent for purifying perfluorocarbon of the present invention can be obtained as an adsorbent controlled in the micropore size through the above-described treatment steps.

The original coal used in the production of the adsorbent for purifying perfluorocarbon of the present invention can be at least one member selected from the group consisting of coconut husk coal, coal, charcoal and tar pitch. On taking account of the denseness of char necessary for the growth of micropores and the hardness as an adsorbent, coconut husk coal is preferably used. The carbonization temperature of the original coal is not particularly limited, however, those obtained by a carbonization treatment at 400 to 600° C., preferably at 400 to 500° C., which are almost free of growing of micropores, are preferred.

The treatment steps are described below in sequence of the step (1) of washing the selected original coal with an acid and then with water, the step (2) of performing the deoxidization and/or dehydration, the step (3) of performing the re-carbonization and the step (4) of performing the activation.

The step (1) of washing an original coal with an acid and then with water is a step performed for removing the metal moiety, particularly alkali metals, contained in the original coal. The metal moiety, particularly alkali metals, contained in the original coal acts as a catalyst in the activation treatment step (4) and accelerates the reaction of activating gases (water vapor and carbon dioxide) with carbon atoms in the original coal and this makes it difficult to control the micropore size. Therefore, in order to remove the metal moiety, particularly alkali metals, the washing step (1) with an acid and water is performed.

Examples of the acid which can be used in the acid washing of the step (1) include mineral acids such as hydrochloric acid, sulfuric acid, nitric acid and phosphoric acid, and organic acids such as acetic acid and trifluoroacetic acid. Among these, preferred are mineral acids, more preferred are hydrochloric acid and/or sulfuric acid, and on taking account of the metal salts produced, still more preferred is hydrochloric acid. With respect to the acid concentration, if the concentration is too low, the effect of removing metals is reduced, whereas if it is excessively high, the effect is saturated. Therefore, the acid concentration is suitably from 1 to 1,000 mol/m$^3$, preferably from 200 to 500 mol/m$^3$. With respect to the ratio of the acid solution used for the acid washing to the original coal, similarly to the acid concentration, if the ratio is too small, the effect of removing metals is not provided, whereas if it is excessively large, the effect is saturated. Therefore, the ratio is, in terms of the volume ratio, suitably from 1:1 to 5:1, preferably from 1:1 to 2:1.

The washing time may be on the order of a few hours when the washing temperature is high. Even when the washing temperature is low of around room temperature, the metal moiety contained in the original coal may be satisfactorily washed by allowing the original coal to stand approximately a whole day and night. The water washing treatment performed after the acid washing treatment is a washing treatment performed for not allowing metal salts dissolved out from the original coal to remain in the original coal and the washing method therefor is not particularly limited. For example, thorough washing may be attained by either a continuous system or a batch system, using water having a small metal salt content, such as clean water. The completion of washing can be known by a pH (pH: 3 to 5) of the washing solution after the washing.

The operation of drying the original coal passed through the water washing may be independently performed before the deoxidization and/or dehydration step (2) or may be performed in the step (2). The step (2) is a step performed for purging oxygen gas and moisture so as to reduce the effect of the oxygen source in the re-carbonization treatment step (3). Various inert gases can be used as the purging gas and among those, nitrogen gas is preferred. The flow rate and the treatment time of the purging gas are not particularly limited, and an appropriate gas flow rate and an appropriate treatment time may be selected so that the oxygen gas and moisture released from the original coal can be smoothly discharged out of the system. The temperature in the step (2) is lower than the temperature in the re-carbonization treatment step (3) so as to attain swift elevation to the carbonization temperature of the step (3) and at the same time, the temperature is constant and suitably from 50 to 250° C., preferably from 100 to 250° C., where re-carbonization does not occur. In the case of starting from the above-described original coal washed using at least the method of step (1), the adsorbent for purifying perfluorocarbon of the present invention can be produced by a method comprising the steps (2) to (4).

The re-carbonization treatment step (3) is performed for dry distilling under heating the original coal from which metals are removed in the step (1), and thereby causing decomposition of the tar moiety, generation and growing of carbonization macropores, and at last carbonization of the tar moiety. This step has a close relationship with the generation and growing of micropores in the activation treatment step (4) and therefore, the temperature conditions in the step (3) must be prudently selected. If the temperature rising rate at the transition from the step (2) to the step (3) is low, the tar moiety may not be removed as a volatile matter upon dry distillation and macropores may not grow. The temperature rising rate is preferably higher and may be from 300 to 500° C./hr. During the temperature rising, the treatment is preferably performed in an inert gas stream.

In the step (3) of performing the re-carbonization treatment, if the temperature is low, volatile components cannot be thoroughly removed and the micropore distribution is broadened, whereas if the temperature is high, the carbon substrate shrinks to cause shrinkage of micropores. Therefore, the re-carbonization treatment is suitably performed at a temperature of from 500 to 700° C., preferably from 600 to 700° C. The re-carbonization treatment time may be from 1 to 2 hours for the above-described purpose. The re-carbonization treatment is performed in an inert gas stream and various inert gases can be used as the inert gas. Among those, nitrogen gas is preferred. The flow rate of the inert gas is suitably from 2 to 10 L/min, preferably from 3 to 5 L/min, per 1 L of the original coal treated.

The activation treatment step (4) is a step of reacting the original coal re-carbonized in the step (3) with a gas to grow micropores and this step proceeds through a first step of opening the closed micropores within the crystal body and a second step of forming micropores having a large size resulting from the complete disappearance of walls between adjacent micropores.

In the step (4), the conditions such as treating gas composition, temperature and time must be prudently selected. With respect to the kind of the treating gas in the activation treatment step (4), air (oxygen) is disadvantageous. The reason therefor is that the reaction thereof with carbons in the original coal is accompanied by the generation of huge heat and therefore, the temperature in the furnace cannot be controlled, as a result, partial overheating is caused and uniform activation cannot be attained. The water vapor also relatively vigorously reacts with the carbons and therefore, if the water vapor is used alone, the micropore size cannot be controlled in the activation treatment step. Therefore, the water vapor must be mixed with carbon dioxide which reacts with the carbons relatively more gently than the water vapor, or with nitrogen which is an inert gas, so that a gentle reaction can proceed. To this purpose, a mixed gas containing an inert gas such as nitrogen, carbon dioxide and water vapor can be used.

With respect to the ratio of each component in the mixed gas, the water vapor which vigorously reacts with carbon is preferably in a smaller ratio. The mixed gas comprising an inert gas, carbon dioxide and water vapor preferably contains from 50 to 89 vol % of the inert gas, from 10 to 30 vol % of carbon dioxide and from 1 to 20 vol % of water vapor, more preferably contains from 70 to 80 vol % of nitrogen gas, from 15 to 25 vol % of carbon dioxide and from 2 to 10 vol % of water vapor. The flow rate of the mixed gas is suitably from 0.5 to 3 L/min, preferably from 1 to 2 L/min, per 1 L of the original coal treated.

The steps (2) to (4) each is performed under heating and therefore, these steps are preferably performed continuously. Particularly, the step (3) and the step (4) which are the treatments under a higher temperature, are preferably performed continuously. At the transition from the step (3) to the step (4), if the temperature rising rate is low, the closed micropores within the carbon crystal body are not opened and the surface area does not increase, whereas if the temperature rising rate is high, the specific surface area and the micropore size are liable to increase excessively. Therefore, the temperature rising rate at the transition from the step (3) to the step (4) is preferably from 100 to 200° C./hr.

If the temperature in the activation treatment step (4) is low, opening and enlargement of micropores do not satisfactorily proceed, whereas if it is high, the control thereof is difficult. Accordingly, the temperature in the activation treatment step is suitably from 700 to 900° C., preferably from 800 to 900° C. As the treatment time is prolonged, the micropore size of activated carbon becomes larger due to the progress of activation and therefore, the treatment time can be determined according to the size of impurities which are the object of removal by adsorption. For example, in order to adsorb impurities contained in FC-218 or FC-C318 which is one object of the present invention, the treatment time may be selected from the range of 1 to 20 hours. The treatment time is preferably from 5 to 18 hours.

After the step (4), the activated coal is cooled to room temperature in an inert gas stream and the temperature falling rate therefor is preferably as high as possible. The temperature falling rate can be selected from the range of 200 to 300° C./hr. If the temperature falling rate is low, the lowering of the temperature takes a time and the adsorbent controlled in the micropore size is disadvantageously liable to undergo changes in the micropores. The flow rate of the inert gas is preferably higher in order to smoothly remove the heat of the adsorbent out of the system but may be selected from the range of 1.5 to 3 L/min per 1 L of the coal treated.

By using the method described above, the adsorbent for purifying perfluorocarbon of the present invention can be produced. The adsorbent obtained is characterized by the small content particularly of alkali metals because the original coal is washed with an acid and with water. The total amount of alkali metals contained in the adsorbent is 1,000 ppm or less. In particular, the potassium content is 500 ppm or less, preferably 200 ppm or less. For measuring the alkali metal content of the adsorbent, for example, a method of ashing the adsorbent, dissolving it in an acid and measuring the solution by an ICP measurement may be used. The iodine adsorption quantity is from 700 to 1,000 mg/g. The iodine adsorption quantity can be determined by a measuring method according to JIS K 1474.

The adsorbent for purifying perfluorocarbon of the present invention can be used as an adsorbent for purifying FC-218 and FC-C318 among perfluorocarbons, and can effectively adsorb and thereby remove the above-described chlorine-type impurities contained in these perfluorocarbons.

A process for purifying FC-218 or FC-C318 using the adsorbent produced by the above-described method is described below.

As described above, crude FC-218 contains, as impurities, particularly at least one compound selected from the group consisting of CFC-115, FC-1216, etc., and FC-C318 contains, as impurities, at least one compound selected from the group consisting of HCFC-124, HCFC-124a, CFC-114, HFC-227ca and FC-1216, and the content of the impurities of FC-218 or FC-C318 is generally from 10 to 10,000 ppm. The process for purifying perfluorocarbon such as FC-218 or FC-C318 of the present invention can use a known method, for example, a flow method using a fixed bed. A contact process using the flow method is preferred because a continuous treatment can be performed. The phase contacted may be a gas phase or a liquid phase and in either case, impurities can be effectively removed from FC-218 or FC-C318.

The linear velocity of FC-218 or FC-C318 based on the adsorbent is from 1 to 10 m/min, preferably from 2 to 5 m/min, in the case of the gas phase contact process, and from 0.2 to 5 m/hr, preferably from 0.5 to 2 m/hr, in the case of the liquid phase contact process. In both the gas phase contact process and the liquid phase contact process, if the linear velocity is higher than the above-described range, the adsorption band becomes long and the time until the break through becomes short, as a result, the adsorption capacity is liable to decrease, whereas even if the linear velocity is lower than that range, the adsorption capacity is not improved but on the contrary, the treatment disadvantageously takes a long time. The temperature at the purification treatment using the adsorbent of the present invention can be around room temperature and specific cooling or heating may not be performed. The pressure may be from 0 to 3 MPa, preferably 0 to 1 MPa in terms of the gauge pressure and the treatment can be performed under a normal pressure which is easy to handle. An operation such as pressurization is not necessary.

When the adsorption capacity is saturated, the adsorbent may be regenerated and then used. In regenerating the adsorbent, the impurities including FC-218 or FC-C318 can be desorbed by passing an inert gas through the adsorbent at an elevated temperature and nitrogen may be used as the inert gas. The regenerating temperature is suitably from 100 to 400° C., more preferably from 100 to 200° C.

As described above, when the purification process of the present invention is used, high-purity FC-218 or FC-C318 can be obtained. Accordingly, for example, when chlorodifluoromethane is thermally decomposed to obtain crude octafluoropropane or octafluorocyclobutane in the step (I) and the crude octafluoropropane or octafluorocyclobutane obtained in the step (I) is purified by contacting it with the adsorbent for purifying perfluorocarbon of the present invention in the step (II), high-purity FC-218 or FC-C318 can be produced, The content of impurities contained in crude FC-218 or FC-C318 is usually from 10 to 10,000 ppm, on the other hand, the purity of FC-218 or FC-C318 obtained by the production process of the present invention is 99.9999% by mass or more. Here, the purity of FC-218 or FC-C318 is defined as a value obtained by subtracting the halocarbon portions except for FC-218 or FC-C318 from 100% by mass. For the analysis of FC-218 or FC-C318 having a purity of 99.9999% by mass or more, (1) gas chromatography (GC) using TCD, FID (each including precut method) or ECD or (2) an analysis instrument such as gas chromatography-mass spectrometer (GC-MS) may be used.

The high-purity FC-218 and FC-C318 can be used as an etching gas at the etching step in the process of producing a semiconductor device. Furthermore, the high-purity FC-218 and FC-C318 can be used as a cleaning gas at the cleaning step in the process of producing a semiconductor device. In the production process of a semiconductor device such as LSI and TFT, a thin or thick film is formed using a CVD method, a sputtering method or a vapor deposition method and the film is etched to form a circuit pattern. In the apparatus for forming the thin or thick film, cleaning is performed to remove unnecessary deposits accumulated on the inner wall of the apparatus, jig and the like, because unnecessary deposits cause generation of particles and must be removed on occasion for producing a good-quality film.

In the etching method using FC-218 or FC-C318, the etching may be performed under various dry etching conditions such as plasma etching and microwave etching. The FC-218 or FC-C318 may also be used by mixing it with an inert gas such as He, $N_2$ and Ar, or with a gas such as HCl, $O_2$ and $H_2$, at an appropriate ratio.

EXAMPLES

The present invention is described in greater detail below by referring to the Examples and Comparative Examples, however, the present invention should not be construed as being limited to these Examples.

Example 1

75 L of coconut husk coal (grown in Philippine) was washed with hydrochloric acid having a concentration of 300 mol/m³ and thereafter, a water washing operation was repeated three times. The amount used of hydrochloric acid having a concentration of 300 mol/m³ was the same as the volume amount of the original coal washed and after adding the hydrochloric acid to the original coal, the original coal was allowed to stand for 15 hours and then deliquefied. The amount of water at the water washing was 5 times the volume amount of the original coal and the completion of washing was confirmed by the point where the pH of the washing solution after the washing became 4.

The metal concentrations in the original coal were analyzed after and before the acid washing and the results are shown in Table 3.

TABLE 3

Analysis of Metals in Original Coal
Metal Content (ppm by mass)

| Component | Before Acid Washing | After Acid Washing |
|---|---|---|
| Na | 812 | 119 |
| K | 4950 | 132 |
| Ca | 462 | 112 |
| Fe | 837 | 103 |
| Al | 876 | 100 |

As is apparent from the measurement results of metal contents shown in Table 3, the contents of metals in the original coal can be reduced by performing the acid washing. Particularly, among alkali metals which are substances of inhibiting the control of micropore size, the content of potassium can be reduced.

Thereafter, the original coal was charged into a kiln (metal rotary kiln using an electric external heating system, revolution number: 8 rpm, internal diameter of kiln: 950 mm, cylindrical part: 620 mm, 50 kw, 150 A (max)) and dried with nitrogen at 90° C. for two hours. The nitrogen used had a purity of 99% or more and the flow rate thereof was 50 L/min. The dried original coal was treated in the above-described kiln through the steps (2) to (4) under the conditions shown in Table 4.

TABLE 4

| Stage | Step | Temperature (° C.) | Time (hr) | $N_2$ (L/min) | $CO_2$ (L/min) | $H_2O$ (L/min) |
|---|---|---|---|---|---|---|
| 1 | deoxidization/dehydration | 150 | 2 | 50 | 0 | 0 |
| 2 | | 150→650 rising | 1 | 300 | 0 | 0 |
| 3 | re-carbonization | 650 | 2 | 300 | 0 | 0 |
| 4 | | 650→850 rising | 1 | 72 | 20 | 8 |
| 5 | activation | 850 | 16 | 72 | 20 | 8 |
| 6 | | 850→600 falling | 1 | 72 | 20 | 8 |
| 7 | | 600→ falling | 1 | 100 | 0 | 0 |

Example 2

Into an adsorption tower of 11 mm (internal diameter)× 100 cm (tower height), 55 g of the adsorbent obtained by performing the treatments until activation in the same manner as in Example 1 was packed, and impurities contained in FC-218 were adsorbed. For removing water and volatile matters in the adsorbent, the adsorbent was previously treated for 8 hours in total in a nitrogen stream (>1 L/min) at 60° C. for 1 hour and at 160° C. for 7 hours. Using this adsorbent, FC-218 containing 400 ppm by mass of CFC-115 and 600 ppm by mass of FC-1216 was passed through the adsorbent in a gas phase at room temperature under pressure of 0.7 MPa at a linear velocity of 1 m/min, and thereby the impurities were adsorbed. The amounts of impurities before and after the treatment with the adsorbent were determined by gas chromatography. The analysis conditions in the gas chromatography are shown below.

| | |
|---|---|
| Instrument Body: | GC-14B (manufactured by Shimadzu Seisakusho K.K.) |
| Carrier: | He gas |
| Detector: | flame ionization detector (FID) |
| Amount of sample: | 0.2 ml |
| Method of determination: | absolute calibration curve |

CFC-115 and FC-1216 in FC-218 were analyzed at the adsorption tower outlet after the passing of 50, 100, 150 and 200 minutes from the initiation of flowing of FC-218 and the results are shown in Table 5. In either impurity substance, the impurity concentration at the adsorption tower outlet was found to be 1 ppm by mass or less after the passing of 200 minutes. It is seen from these results that by contacting an adsorbent obtained through a series of activation treatments with FC-218 containing the above-described impurities, the impurities can be effectively adsorbed and separated and thereby FC-218 can be purified to a high purity.

Comparative Example 1

The same activation treatments as in Example 1 were performed except for not performing the step of acid-washing and water-washing the coconut husk coal used as the original coal in Example 1. Using the obtained adsorbent, a treatment of adsorbing impurities in FC-218 was performed in the same manner as in Example 2. The amounts of impurities before and after the treatment with the adsorbent were determined in the same manner by gas chromatography. CFC-115 and FC-1216 in FC-218 were analyzed at the adsorption tower outlet after the passing of 50 and 100 minutes from the initiation of flowing of FC-218 and the results are shown in Table 5. FC-1216 was adsorbed and separated in the same manner as in Example 2, however, CFC-115 was already broken through after the passing of 50 minutes.

It is seen from these results that when the step of performing the acid washing and water washing is omitted out of the steps of treating original coal, the micropore size of activated carbon cannot be controlled and CFC-115 cannot be adsorbed and separated.

Comparative Examples 2 and 3

The impurities in FC-218 were adsorbed in the same manner as in Example 2 except for using 46 g of MORS-IEBON X2M/6 (commonly MSC-5A) produced by Takeda Yakuhin Kogyo K. K. (Comparative Example 2) or 57 g of coconut husk activated carbon Y-10 produced by Ajinomoto Fine Techno K. K. (Comparative Example 3) as the adsorbent in place of the adsorbent of Comparative Example 1. The amounts of impurities before and after the treatment with the above-described activated carbon were determined in the same manner by gas chromatography. CFC-115 and FC-1216 in FC-218 were analyzed at the adsorption tower outlet after the passing of 50 and 100 minutes from the initiation of flowing of FC-218 and the results are shown in Table 5. FC-1216 was adsorbed and separated in the same manner as in Example 2, however, CFC-115 was already broken through after the passing of 50 minutes. It is found that these commercially available adsorbents are inferior in the ability of adsorbing CFC-115 as compared with the adsorbent obtained by the method of Example 1.

TABLE 5

| | Change in Concentration of Each Impurity | | |
|---|---|---|---|
| | | Composition (ppm by mass) | |
| | Time (min) | CFC-115 | FC-1216 |
| Example 2 | 0 (sample fed) | 400 | 600 |
| | 50 | 0 | 0 |
| | 100 | 0 | 0 |
| | 150 | 0 | 0 |
| | 200 | 0 | 0 |
| Comparative Example 1 | 50 | 50 | 0 |
| | 100 | 165 | 0 |
| Comparative Example 2 (MSC-5A) | 50 | 12 | 0 |
| | 100 | 40 | 0 |
| Comparative Example 3 (Y-10) | 50 | 65 | 0 |
| | 100 | 170 | 0 |

The volumes of respective impurities adsorbed based on each adsorbent used in Example 2 and Comparative Examples 1 to 3 are shown in Table 6. The volume of impurity adsorbed was calculated by setting the break point at the point where the concentration of impurity in gas at the adsorption tower outlet exceeds 1 ppm by mass, determining the volume of each impurity until the break point was reached, and dividing the determined value by the weight of the adsorbent used. On comparison between the adsorbent used in Example 2 with the adsorbents of Comparative Examples 1 to 3, it is seen that the adsorbent used in Example 2 is improved in the volume of impurities adsorbed more than the adsorbents in Comparative Examples.

TABLE 6

| | Volume Adsorbed (g/kg (adsorbent)) | |
|---|---|---|
| | CFC-115 | FC-1216 |
| Example 2 | 1.6 | 55 |
| Comparative Example 1 | <0.1 | 6 |
| Comparative Example 2 | 0.1 | 6 |
| Comparative Example 3 | <0.1 | 5 |

Example 3

Into an adsorbent tower of 22 mm (internal diameter)×60 cm (tower height), 101 g of the same adsorbent as used in Example 2 was packed and treated at 120° C. for 2 hours and at 150° C. for 4 hours in a helium stream. Using the adsorbent, FC-218 containing 600 ppm by mass of only FC-1216 was passed through the adsorbent at room temperature under pressure of 0.7 MPa at a linear velocity of 5 m/min in a gas phase, thereby allowing the impurities to be adsorbed. The amount of the impurity before and after the treatment with the adsorbent was determined in the same manner by gas chromatography. The break point was determined in the same manner as in Example 2 and the volume of FC-1216 adsorbed was calculated. The results are shown in Table 7.

Comparative Examples 4 to 6

FC-1216 was adsorbed in the same manner as in Example 3 except for using 104 g of coconut husk activated carbon Y-10 (Comparative Example 4), 94 g of granular coal-type activated carbon CL-H (produced by Ajinomoto Fine Techno K. K.) (Comparative Example 5) or 91 g of MSC-5A (Comparative Example 6) as the adsorbent in place of the adsorbent of Example 3. The amount of the impurity before and after the treatment with the adsorbent was determined in the same manner by gas chromatography. The volume of FC-1216 adsorbed was calculated in the same manner as in Example 2. The results are shown in Table 7.

TABLE 7

| | Volume Adsorbed (g/kg (adsorbent)) FC-1216 |
|---|---|
| Example 3 | 180 |
| Comparative Example 4 | 25 |
| Comparative Example 5 | 8 |
| Comparative Example 6 | 25 |

It is seen from the results of Example 3 and Comparative Examples 4 to 6 that conventional activated carbon-type adsorbents are certainly effective for the adsorption of FC-1216 as a sole impurity, however, the volume of the impurity adsorbed by the adsorbent of the present invention is as high as about 10 times and this reveals that the adsorbent of the present invention is extremely improved and more effective than conventional adsorbents.

Example 4

Into an adsorption tower of 11 mm (internal diameter)× 200 cm (tower height), 110 g of the adsorbent obtained by performing the treatments until activation in the same manner as in Example 1 was packed. At the beginning, for removing water and volatile matters in the adsorbent, the adsorbent was treated for 6 hours in total in a nitrogen stream (flow rate: >5 L/min) at 120° C. for 2 hour and then at 150° C. for 4 hours before performing the adsorption treatment. With this adsorbent, FC-C318 containing 200 ppm by mass of FC-1216, 50 ppm by mass of HCFC-124, 50 ppm by mass of HCFC-124a, 100 ppm by mass of HFC-227ca and 200 ppm by mass of CFC-114 was contacted in a gas phase under conditions of room temperature, a pressure of 0.2 MPa and a linear velocity of 2.5 m/min, thereby performing the treatment of adsorbing impurities. The amounts of impurities before and after the treatment with the adsorbent were quantitated by gas chromatography. The analysis conditions in the gas chromatography are shown below.

| | |
|---|---|
| Instrument body: | GC-14B (manufactured by Shimadzu Seisakusho K.K.) |
| Carrier: | He gas |
| Detector: | flame ionization detector (FID) |
| Amount of sample: | 1 ml |
| Method of quantitation: | simple area percentage (%) |

The analysis results of FC-1216, HCFC-124, HCFC-124a, HFC-227ca and CFC-114 in FC-C318 at the adsorption tower outlet after the passing of 25, 50, 75, 100 and 125 hours from the initiation of flowing of FC-C318 are shown in Table 8. Any impurity substance was found to have a concentration of 1 ppm by mass or less after the passing of 125 hours. It is seen from these results that by contacting FC-C318 containing those impurities with an adsorbent obtained through a series of activation treatments, the impurities can be adsorbed and separated and thereby a high-purity FC-C318 can be obtained.

Comparative Example 7

The same treatments as in Example 1 were performed except that the coconut husk coal used as the original coal in Example 1 was not washed with an acid and water. Using the obtained adsorbent, a treatment of adsorbing impurities was performed in the same manner as in Example 4. The amounts of impurities before and after the treatment with the adsorbent were quantitated in the same manner by gas chromatography. The analysis results of FC-1216, HCFC-124, HCFC-124a, HFC-227ca and CFC-114 in FC-C318 at the adsorption tower outlet after the passing of 25 and 50 hours from the initiation of flowing of FC-C318 are shown in Table 8. As is apparent from the results shown in Table 8, any impurity exceeded a concentration of 10 ppm by mass after the passing of 25 hours and already reached the break through, and this clearly reveals that the adsorbent was inferior in the capacity of adsorbing impurities as compared with the adsorbent obtained by the method of Example 1. From these results, it is seen that when the step of washing the original coal with an acid and then with water is omitted from the treatment steps, the micropore size of the adsorbent cannot be controlled and impurities cannot be separated by adsorption.

Comparative Examples 8 and 9

A treatment of adsorbing impurities was performed in the same manner as in Example 4 except for using 99 g of MORSIEBON X2M4/6 (common name: MSC-5A, produced by Takeda Yakuhin Kogyo K. K.) (Comparative Example 8) or 107 g of coconut husk activated carbon Y-10 (produced by Ajinomoto Fine Techno K. K.) (Comparative Example 9) as the adsorbent in place of the adsorbent of Comparative Example 7. The amounts of impurities before and after the treatment with the above-described activated carbon were quantitated in the same manner by gas chromatography. The analysis results of FC-1216, HCFC-124, HCFC-124a, HFC-227ca and CFC-114 in FC-C318 at the adsorption tower outlet after the passing of 25 and 50 hours from the initiation of flowing of FC-C318 in the same manner as in Comparative Example 7 are shown in Table 8. Similarly to Comparative Example 7, any substance exceeded a concentration of 10 ppm by mass after the passing of 25 hours and already reached the break through. This reveals that the adsorbents are inferior in the capacity of adsorbing impurities as compared with the adsorbent obtained by the method of Example 1 and the impurities cannot be satisfactorily separated by adsorption similarly to Comparative Example 7.

TABLE 8

| | | Change in Concentration of Each Impurity | | | | |
|---|---|---|---|---|---|---|
| | Time | Composition (ppm by mass) | | | | |
| | (hr) | FC-1216 | HCFC-124 | HCFC-124a | HFC-227ca | CFC-114 |
| Example 4 | 0 (sample fed) | 200 | 50 | 50 | 100 | 200 |
| | 25 | 0 | 0 | 0 | 0 | 0 |
| | 50 | 0 | 0 | 0 | 0 | 0 |
| | 75 | 0 | 0 | 0 | 0 | 0 |
| | 100 | 0 | 0 | 0 | 0 | 0 |
| | 125 | 0 | 0 | 0 | 0 | 0 |
| Comparative Example 7 | 25 | 11 | 28 | 30 | 18 | 70 |
| | 50 | 107 | 39 | 40 | 62 | 160 |

TABLE 8-continued

| | | Change in Concentration of Each Impurity | | | | |
|---|---|---|---|---|---|---|
| | Time | Composition (ppm by mass) | | | | |
| | (hr) | FC-1216 | HCFC-124 | HCFC-124a | HFC-227ca | CFC-114 |
| Comparative Example 8 (MSC-5A) | 25 | 11 | 34 | 32 | 16 | 116 |
| | 50 | 96 | 45 | 40 | 47 | 180 |
| Comparative Example 9 (Y-10) | 25 | 30 | 39 | 41 | 28 | 132 |
| | 50 | 131 | 46 | 47 | 82 | 185 |

The volumes of respective impurities adsorbed to each absorbent used in Example 4 and Comparative Examples 7 to 9 were measured and the results obtained are shown in Table 9. The volumes of impurities adsorbed were calculated by setting the break through to the point where the concentration of each impurity in the gas at the absorption tower outlet exceeds 1 ppm by mass, determining the amount of each impurity adsorbed until the break through was reached, and dividing the obtained value by the weight of the adsorbent used. On comparison between the results of Example 4 with the results of Comparative Examples 7 to 9, it is seen that the absorbent used in Example 4 is extremely improved in the volume of impurities adsorbed more than the adsorbents used in Comparative Examples.

TABLE 9

| | Volume Adsorbed (g/kg (adsorbent)) | | | | |
|---|---|---|---|---|---|
| | FC-1216 | HCFC-124 | HCFC-124a | HFC-227ca | CFC-114 |
| Example 4 | 40 | 40 | 40 | 8 | 15 |
| Comparative Example 7 | 4 | <1 | <1 | 1 | <1 |
| Comparative Example 8 | 4 | <1 | <1 | 2 | <1 |
| Comparative Example 9 | 3 | <1 | <1 | 1 | <1 |

Example 5

Into an adsorbent tower of 22 mm (internal diameter)×60 cm (tower height), 101 g of the adsorbent obtained by performing the treatments until activation in the same manner as in Example 1 was packed and treated at 120° C. for 2 hours and at 150° C. for 4 hours in a helium stream. Using this adsorbent, FC-C318 containing 450 ppm by mass of only FC-1216 was passed in a gas phase through the adsorbent under the conditions of room temperature, a pressure of 0.2 MPa and a linear velocity of 4 m/min. The amount of the impurity before and after the treatment with the adsorbent was quantitated in the same manner by gas chromatography. The break through point of the adsorbent was determined in the same manner and the volume of FC-1216 adsorbed was calculated. The results are shown in Table 10.

Comparative Examples 10 to 12

FC-1216 was adsorbed in the same manner as in Example 5 except for using 104 g of the same activated carbon Y-10 as used in Comparative Example 9 (Comparative Example 10), 94 g of granular coal-type activated carbon CL-H (produced by Ajinomoto Fine Techno K. K.) (Comparative Example 11) or 91 g of the same MSC-5A as used in Comparative Example 8 (Comparative Example 12) as the adsorbent in place of the adsorbent of Example 5. The amount of the impurity before and after the treatment with the adsorbent was quantitated in the same manner by gas chromatography. The volume of FC-1216 adsorbed was calculated in the same manner as in Example 5 and the results obtained are shown in Table 10.

TABLE 10

| | Volume Adsorbed (g/kg (adsorbent)) FC-1216 |
|---|---|
| Example 5 | 200 |
| Comparative Example 10 | 30 |
| Comparative Example 11 | 10 |
| Comparative Example 12 | 30 |

It is seen from the results of Example 5 and Comparative Examples 10 to 12 that conventional activated carbon-type adsorbents are effective in adsorbing FC-1216 as a sole impurity, however, the volume of the impurity adsorbed by the adsorbent of the present invention is as high as about 10 times the volumes by conventional activated carbons and this reveals that the adsorbent of the present invention is extremely improved and more effective than conventional adsorbents.

APPLICABILITY TO THE INDUSTRY

As described in the foregoing pages, when the process for producing FC-218 and FC-C318 of the present invention is used, high-purity FC-218 and FC-C318 can be obtained, and the high-purity FC-218 and FC-C318 produced using the present invention can be used as an etching or cleaning gas in the process of manufacturing a semiconductor device.

The invention claimed is:

1. An adsorbent for purifying a perfluorocarbon, which is produced using a method comprising the following four steps:
   (1) washing an original coal with an acid and then with water;
   (2) deoxidizing and/or dehydrating the original coal obtained in the step (1) at a temperature of 50 to 250° C. in an inert gas stream;
   (3) re-carbonizing the original coal obtained in the step (2) at a temperature of from 500 to 700° C. in an inert gas stream; and
   (4) activating the original coal obtained in the step (3) at a temperature of 700 to 900° C. in a mixed gas stream containing an inert gas, carbon dioxide and water vapor,
   wherein the total content of alkali metals in the adsorbent is 1,000 ppm or less.

2. The adsorbent for purifying a perfluorocarbon as claimed in claim 1, wherein the original coal is obtained by carbonizing at least one member selected from the group consisting of coconut husk coal, coal, charcoal and tar pitch at a temperature of 400 to 600° C.

3. The adsorbent for purifying a perfluorocarbon as claimed in claim 1, wherein the acid used in the acid washing of the step (1) is a mineral acid and the acid concentration is from 1 to 1,000 mol/m$^3$.

4. The adsorbent for purifying a perfluorocarbon as claimed in any one of claims 1 to 3, wherein the acid used in the acid washing of the step (1) is hydrochloric acid and/or sulfuric acid.

5. The adsorbent for purifying a perfluorocarbon as claimed in claim 1, wherein the step (3) is performed by elevating the temperature up to the re-carbonization temperature of the step (3) at a rate of from 300 to 500° C./hr in an inert gas stream after the step (2).

6. The adsorbent for purifying a perfluorocarbon as claimed in claim 1, wherein the step (4) is performed by elevating the temperature up to the activation temperature of the step (4) at a rate of from 100 to 200° C./hr in an inert gas stream after the step (3).

7. The adsorbent for purifying a perfluorocarbon as claimed in claim 1, wherein in the step (4), the mixed gas containing an inert gas, carbon dioxide and water vapor contains from 50 to 89 vol % of the inert gas, from 10 to 30 vol % of carbon dioxide and from 1 to 20 vol % of water vapor.

8. The adsorbent for purifying a perfluorocarbon as claimed in claim 1, wherein the activated coal is cooled to room temperature at a rate of from 200 to 300° C./hr in an inert gas stream after the step (4).

9. The adsorbent for purifying a perfluorocarbon as claimed in claim 1, wherein the iodine adsorption quantity of the adsorbent is from 700 to 1,000 mg/g.

10. The adsorbent for purifying a perfluorocarbon as claimed in claim 1, wherein the potassium content in the adsorbent is 500 ppm or less.

11. The adsorbent for purifying a perfluorocarbon as claimed in claim 1, wherein the perfluorocarbon is octafluoropropane.

12. The adsorbent for purifying a perfluorocarbon as claimed in claim 1, wherein the perfluorocarbon is octafluorocyclobutane.

13. A process for producing an adsorbent for purifying a perfluorocarbon, comprising the following four steps;
   (1) washing an original coal with an acid and then with water;
   (2) deoxidizing and/or dehydrating the original coal obtained in the step (1) at a temperature of from 50 to 250° C. in an inert gas stream;
   (3) re-carbonizing the original coal obtained in the step (2) at a temperature of 500 to 700° C. in an inert gas stream; and
   (4) activating the original coal obtained in the step (3) at a temperature of from 700 to 900° C. in a mixed gas stream containing an inert gas, carbon dioxide and water vapor.

14. The process for producing an adsorbent for purifying a perfluorocarbon as claimed in claim 13, wherein the original coal is obtained by carbonizing at least one member selected from the group consisting of coconut husk coal, coal, charcoal and tar pitch at a temperature of from 400 to 600° C.

15. The process for producing an adsorbent for purifying a perfluorocarbon as claimed in claim 13, wherein the acid used in the acid washing of the step (1) is a mineral acid and the acid concentration is from 1 to 1,000 mol/m$^3$.

16. The process for producing an adsorbent for purifying a perfluorocarbon as claimed in any one of claims 13 to 15, wherein the acid used in the acid washing of the step (1) is hydrochloric acid and/or sulfuric acid.

17. The process for producing an adsorbent for purifying a perfluorocarbon as claimed in claim 13, wherein the step (3) is performed by elevating the temperature up to the re-carbonization temperature of the step (3) at a rate of from 300 to 500° C./hr in an inert gas stream after the step (2).

18. The process for producing an adsorbent for purifying a perfluorocarbon as claimed in claim 13, wherein the step (4) is performed by elevating the temperature up to the activation temperature of the step (4) at a rate of from 100 to 200° C./hr in an inert gas stream after the step (3).

19. The process for producing an adsorbent for purifying a perfluorocarbon as claimed in claim 13, wherein in the step (4), the mixed gas containing an inert gas, carbon dioxide and water vapor contains from 50 to 89 vol % of the inert gas, from 10 to 30 vol % of carbon dioxide and from 1 to 20 vol % of water vapor.

20. The process for producing an adsorbent for purifying a perfluorocarbon as claimed in claim 13, wherein the activated coal is cooled to room temperature at a rate of from 200 to 300° C./hr in an inert gas stream after the step (4).

21. The process for producing an adsorbent for purifying a perfluorocarbon as claimed in claim 13, wherein the iodine adsorption quantity of the adsorbent is 700 to 1,000 mg/g.

22. The process for producing an adsorbent for purifying a perfluorocarbon as claimed in claim 13, wherein the total content of alkali metals in the adsorbent is from 1,000 ppm or less.

23. The process for producing an adsorbent for purifying a perfluorocarbon as claimed in claim 22, wherein the potassium content of the adsorbent is 500 ppm or less.

24. The process for producing an adsorbent for purifying a perfluorocarbon as claimed in claim 13, wherein the perfluorocarbon is octafluoropropane or octafluorocyclobutane.

25. A process for purifying octafluoropropane, comprising contacting crude octafluoropropane containing from 10 to 10,000 ppm of impurities with the adsorbent for purifying a perfluorocarbon described in claim 1 to purify the crude octafluoropropane.

26. The process for purifying the octafluoropropane as claimed in claim 25, wherein the impurities are at least one compound selected from the group consisting of chloropentafluoroethane, hexafluoropropene and 1H-heptafluoropropane.

27. A process for purifying octafluorocyclobutane, comprising contacting crude octafluorocyclobutane containing from 10 to 10,000 ppm of impurities with the adsorbent for purifying perfluorocarbon described in claim 1 to purify the crude octafluorocyclobutane.

28. The process for purifying the octafluorocyclobutane as claimed in claim 27, wherein the impurities are at least one compound selected from the group consisting of 2-chloro-1,1,1,2-tetrafluoroethane, 1-chloro-1,1,2,2-tetrafluoroethane, 1,2-dichlorotetrafluoroethane, 1H-heptafluoropropane and hexafluoropropene.

29. A process for producing a high-purity octafluoropropane or octafluorocyclobutane, comprising the following steps (I) and (II);
(I) thermally decomposing chlorodifluoromethane to obtain crude octafluoropropane or octafluorocyclobutane; and
(II) contacting the crude octafluoropropane or octafluorocyclobutane obtained in the step (I) with the adsorbent for purifying perfluorocarbon described in claim 1 to purify the crude octafluoropropane or octafluorocyclobutane.

30. The process for producing high-purity octafluoropropane or octafluorocyclobutane as claimed in claim 29, wherein the purity of the purified octafluoropropane or octafluorocyclobutane is 99.9999% by mass or more.

* * * * *